United States Patent [19]

Clark et al.

[11] Patent Number: 5,382,673

[45] Date of Patent: Jan. 17, 1995

[54] PROCESS FOR PREPARING FLORFENICOL, ITS ANALOGS AND OXAZOLINE INTERMEDIATES THERETO

[75] Inventors: Jon E. Clark, Highland Park; Doris P. Schumacher, Florham Park; Guang-Zhong Wu, Somerville, all of N.J.

[73] Assignee: Schering Corporation, Kenilworth, N.J.

[21] Appl. No.: 39,450

[22] PCT Filed: Oct. 23, 1991

[86] PCT No.: PCT/US91/07608

§ 371 Date: Apr. 22, 1993

§ 102(e) Date: Apr. 22, 1993

Related U.S. Application Data

[63] Continuation-in-part of Ser. No. 603,575, Oct. 25, 1990, abandoned.

[51] Int. Cl.[6] .............................................. C07D 263/08
[52] U.S. Cl. ..................................... 548/239; 564/209
[58] Field of Search ........................ 548/237; 564/209

[56] References Cited

U.S. PATENT DOCUMENTS

| | | | |
|---|---|---|---|
| 2,402,198 | 6/1946 | Loder | 548/237 |
| 2,686,787 | 8/1954 | Slack et al. | 546/237 |
| 2,692,897 | 10/1954 | Moersch | 548/237 |
| 2,694,071 | 11/1954 | Jacob et al. | 548/237 |
| 2,718,520 | 9/1955 | Slack et al. | 548/237 |
| 2,759,001 | 8/1956 | Moersch et al. | 548/237 |
| 2,786,870 | 3/1957 | Slack . | |
| 2,820,041 | 7/1958 | Heywood et al. | 548/237 |
| 3,813,378 | 5/1974 | Witte et al. | 548/237 |
| 3,979,405 | 9/1976 | Toth et al. | 548/237 |
| 4,216,162 | 8/1980 | Arit et al. | 548/238 |
| 4,235,892 | 11/1980 | Nagabhushan . | |
| 4,361,557 | 11/1982 | Nagabhushan . | |
| 4,743,700 | 5/1988 | Jommi et al. | 548/216 |
| 4,876,352 | 10/1989 | Schumacher et al. | 548/232 |
| 5,105,009 | 9/1992 | Jommi | 548/232 |
| 5,202,484 | 4/1993 | Villa et al. | 564/302 |
| 5,227,494 | 7/1993 | Schumacher et al. | 548/237 |
| 5,243,050 | 9/1993 | Jommi | 548/232 |

FOREIGN PATENT DOCUMENTS

| | | | |
|---|---|---|---|
| 155135 | 2/1951 | Australia | 548/237 |
| 0130633 | 1/1985 | European Pat. Off. . | |
| 1071077 | 8/1952 | France . | |
| 90-02738 | 3/1990 | WIPO | 548/237 |

OTHER PUBLICATIONS

Chemical Abstracts, 1958, vol. 52, Col. 10180 Abstracting US 3,820,041.

H. Witte and W. Seeliger, Formation of Cyclic Imidic Esters by Reaction of Nitriles etc Ann. Chem. 1974, pp. 996–1009.

Chemical Abstracts, 1956, vol. 50, Col. 13998 Abstracting US 2,718,520.

*Primary Examiner*—Donald G. Daus
*Attorney, Agent, or Firm*—Lee, Jr.: Warrick E.; Joseph T. Majka

[57] ABSTRACT

A process for preparing a compound of formula (IV):

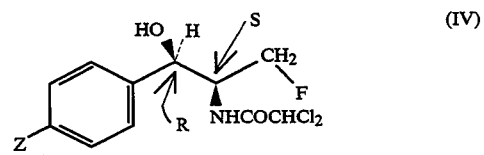

comprising
a) contacting an oxazoline compound of formula (I):

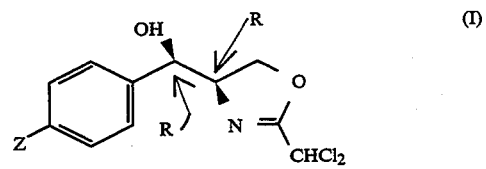

wherein Z is as defined hereinbefore, with a reagent capable of causing an equilibrium between oxazoline compound (I) and an oxazoline compound of formula (II) described herein, and the reagent drives the equilibrium toward oxazoline compound (II) by preferential precipitation of oxazoline compound (II);

b) contacting compound (II) with a fluorinating agent to give a fluorinated oxazoline compound of formula (III) described herein; and c) hydrolyzing the compound of formula (III) to formula (IV). In an alternative embodiment, the process is directed toward a process for preparing oxazoline (II) in a single step.

14 Claims, No Drawings

PROCESS FOR PREPARING FLORFENICOL, ITS ANALOGS AND OXAZOLINE INTERMEDIATES THERETO

The present application is the U.S. national application corresponding to International application No. PCT/US91/07608, filed Oct. 23, 1991 and designating the U.S., which PCT application is in turn a continuation-in-part of U.S. application Ser. No. 07/603,575, filed Oct. 25, 1990 now abandoned the benefits of which applications are claimed pursuant to the provisions of 35 U.S.C. §120,363 and 365 (C).

FIELD OF THE INVENTION

The present invention relates to a novel process for preparing florfenicol, its analogs and oxazoline intermediates thereto.

BACKGROUND OF THE INVENTION

Florfenicol, also known as [R-(R*,S*)]-2,2-dichloro-N-[1-(fluoromethyl)-2-hydroxy-2-[4-(methylsulfonyl)-phenyl]ethylacetamide, is a broad spectrum antibacterial agent useful in the treatment of gram positive, gram negative and rickettsial infections as disclosed in U.S. Pat. No. 4,361,557. The preparation of various oxazoline intermediates of florfenicol have been taught in U.S. Pat. Nos. 4,876,352; 4,743,700 and Patent Cooperation Treaty (PCT) International application No. PCT/US89/03827 having an international filing date of Sep. 12, 1989. Although a number of the above references teach efficient processes for preparing florfenicol, related analogs or processes for preparing their oxazoline intermediates, it would be desirable to provide a process which is even more efficient and economical by using fewer and/or less expensive starting materials, and which is less labor intensive by using fewer man-hours and simpler apparatus.

SUMMARY

In one embodiment, the present invention is directed toward a process for preparing a compound of formula (IV):

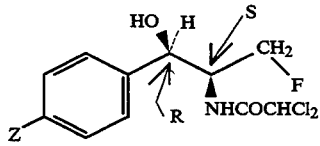

wherein Z represents H, halo, nitro or $H_3CSO_x$—, wherein x is 0, 1 or 2, comprising
a) contacting an oxazoline compound of formula (I):

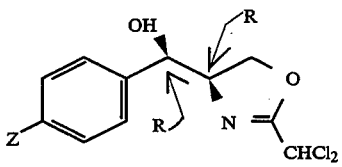

wherein Z is as defined hereinbefore, with a reagent capable of causing an equilibrium between oxazoline compound (I) and an oxazoline compound of formula (II):

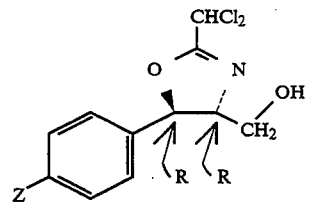

wherein Z is as defined hereinbefore, and the reagent drives the equilibrium toward oxazoline compound (II) by preferential precipitation of oxazoline compound (II);

b) contacting compound (II) with a fluorinating agent to give a fluorinated oxazoline compound of formula (III):

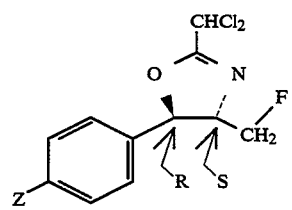

wherein Z is as defined hereinbefore; and
c) hydrolyzing compound (III) to compound (IV).
Each arrow points to a carbon atom which is an asymmetric center giving rise to either the R or S stereoisomer configuration.

In a second embodiment, the present invention is directed towards a process for preparing a fluorinated oxazoline compound of formula (III):

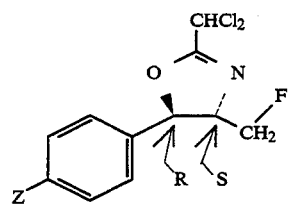

wherein Z represents H, halo, nitro or $H_3CSO_x$—, wherein x is 0, 1 or 2, comprising
a) contacting an oxazoline compound of formula (I):

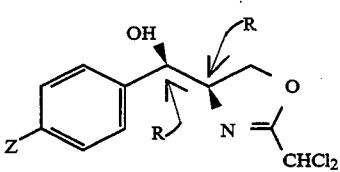

wherein Z is as defined hereinbefore, with a reagent capable of causing an equilibrium between oxazoline compound (I) and an oxazoline compound of formula (II):

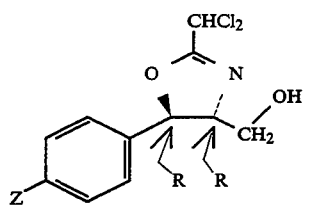

wherein Z is as defined hereinbefore, and the reagent drives the equilibrium toward oxazoline compound (II) by preferential precipitation of oxazoline compound (II); and b) contacting compound (II) with a fluorinating agent to give fluorinated oxazoline compound (III).

In a third embodiment, the present invention is directed toward a process for preparing an oxazoline compound of formula (II):

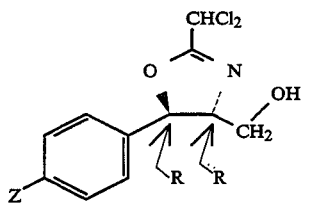

wherein Z represents H, halo, nitro or $H_3CSO_x-$, wherein x is 0, 1 or 2, comprising contacting an oxazoline compound of formula (I):

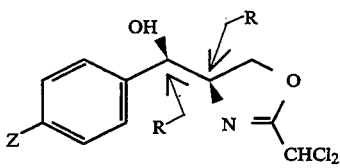

wherein Z is as defined hereinbefore, with a reagent capable of causing an equilibrium between oxazoline compound (I) and oxazoline compound (II), and the reagent drives the equilibrium toward oxazoline compound (II) by preferential precipitation of oxazoline compound (II). The process of this embodiment is equivalent to step (a) of the above processes. Preferably, the equilibrium driving reagent is a protic solvent and ammonia or an ammonium salt. Also preferred is that the protic solvent is isopropanol and the ammonium salt is ammonium acetate.

In another embodiment, oxazoline compound of formula (I) is prepared by contacting an aminodiol of formula (V):

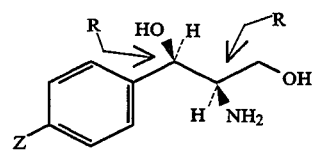

wherein Z is defined hereinbefore, with dichloroacetonitrile and an alcohol, and optionally in the presence of a catalytic amount of an acid, to give a mixture containing oxazoline compounds (I) and (II).

The present invention has the advantage of being more efficient and economical than other processes for preparing florfenicol, its analogs and oxazoline intermediates thereto, by using fewer or less expensive starting materials. Another advantage is that various embodiments of the present process are less labor intensive because they can reduce the amount of time or reduce the need for specialized equipment which would otherwise be required to prepare such compounds.

DETAILED DESCRIPTION OF THE EMBODIMENTS

When utilized in the present specification and in the appended claims the terms listed hereinbelow, unless otherwise indicated are defined as follows:

The term "equilibrium driving reagent" refers to any substance, including mixtures of compounds, which is capable of causing an equilibrium between oxazoline compound (I) and oxazoline compound (II), wherein the reagent drives the equilibrium toward oxazoline compound (II) by preferential precipitation of oxazoline compound (II). That is, in a reaction mixture containing oxazoline compound (I) or a mixture of oxazoline compound (I) and oxazoline compound (II), the equilibrium driving reagent will cause the equilibrium and then drive the equilibrium to favor formation of compound (II) at the desired completion of the reaction, such that the molar ratio of oxazoline compound (II) to oxazoline compound (I) is about 80:20 (II:I), preferably about 90:10, more preferably about 95:5, most preferably about 99:1.

The term "equilibrium" is intended to mean a condition in which the reaction of oxazoline (I) to oxazoline (II) and its opposite or reverse reaction occur at the same rate, resulting in a constant concentration of reactants, as defined in G. G. Hawley (Rev.), The Condensed Chemical Dictionary, 10th Edition, Van Nostrand Reinhold Co., New York, N.Y. (1981 ), 1134 pp.

The term "protic solvent" is intended to mean a hydrogenbonding solvent, as defined in James B. Hendrickson, Cram, Donald J., and Hammond, George S., Organic Chemistry, McGraw Hill Book Company, New York, N.Y., (1970), 1279 pp. The solvent should preferably, but not necessarily, be capable of precipitating oxazoline (II) out of solution. Such solvents include, but are not limited to, water, C-1 to C-10 alkanoic acids such as formic acid (HCOOH), acetic acid and the like, C-1 to C-10 alcohols such as methanol and ethanol, and mixtures thereof. Alternatively, the protic solvent can be admixed with any suitable cosolvent in order to effect precipitation of oxazoline compound (II). Such cosolvents can include other protic solvents or solvents which are miscible with the protic solvent such as C-4 to C-10 alkanes, aromatic solvents such as benzene, toluene, xylenes, halobenzenes such as chlorobenzene, and ethers such as diethylether, tert-butylmethylether and isopropylether, or mixtures of any of the above solvents or cosolvents. When the protic solvent is isopropanol, it is preferably present in the amount illustrated in the examples, that is, about 1.5 to 2 ml of isopropanol per gram of compound (I).

The term "ammonia" refers to the colorless gas defined by the formula $NH_3$. The ammonia can be added as a solution of the gas in a suitable solvent or as the by-product of a previous reaction.

The term "ammonium salt" refers to a salt of the formula $NH_4^+X^-$, wherein $X^-$ is any suitable anion such as chloro, bromo, iodo, sulfate, hydrogen sulfate, phosphate, hydrogen phosphate, dihydrogen phosphate, acetate, propionate, butyrate, isobutyrate, oxalate, benzoate, benzenesulfonate and alkylsulfonates having 1 to 4 carbon atoms in the alkyl group. Alternatively, the ammonia can be admixed with the ammonium salt. The source of the ammonia or ammonium salt can also be generated in-situ, such as in the preparation of oxazoline compound (I) from a cyano reagent and an amino alcohol as described in U.S. Pat. No. 2,759,001, whose preparative teachings are incorporated herein by reference.

The Ishikawa Reagent is 1,1,2,3,3,3-hexylfluro-propyldiethylamine in a methylene chloride solution in a weight ratio of 20 to 60% (weight/weight).

The procedure for preparing these compounds can be represented as follows:

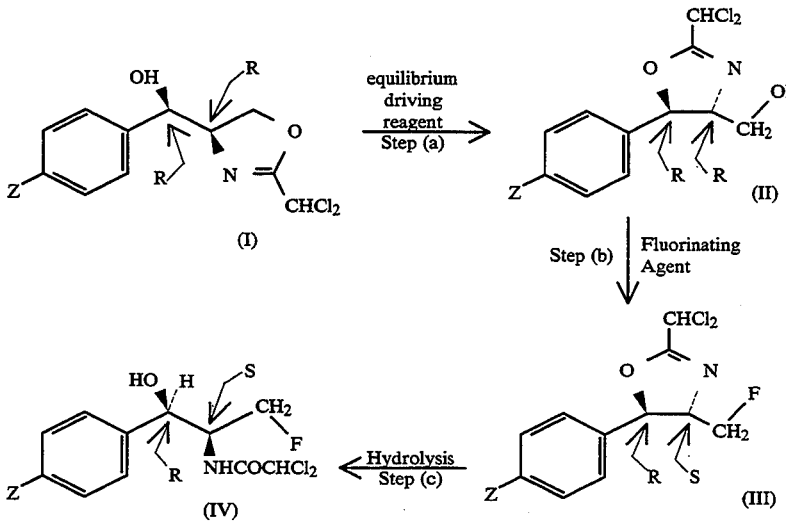

In step (a), oxazoline compound (II) is prepared by contacting oxazoline compound (I) or a mixture of oxazoline compound (I) and oxazoline compound (II) with an equilibrium driving reagent to give oxazoline (II). The ammonia or ammonium salt in the equilbrium driving reagent can be contacted with oxazoline (I) in amounts ranging from excess amounts to about 0.1 mole of ammonia or ammonium salt per mole of oxazoline compound (I), preferably from about two moles to one mole ammonia or ammonium salt, more preferably equimolar amounts of ammonia or ammonium salt to oxazoline compound (I). In carrying out step (a), oxazoline (I) can also be admixed with varying amounts oxazoline (II) before contacting with the equilibrium driving reagent. The contacting of the reactants can be carried out at temperatures ranging from about room temperature to the refluxing temperature of the solvent employed, preferably from about 50 to about 60 degrees Celcius (° C.), at ambient pressures. The reactants can be stirred for a period ranging from about one hour to about 24 hours or more, or until the desired completion of the reaction. The desired precipitated oxazoline compound (II) can be recovered by filtration, centrifugation, drying under vacuum or by removal of any solvents from the reaction mixture.

In step (b), fluorinated oxazoline compound (III) can be prepared by contacting oxazoline compound (II) with a suitable fluorinating agent to give fluorinated oxazoline (III), under conditions as described, for example, in U.S. Pat. No. 4,876,352 whose preparative teachings are incorporated herein by reference. In this procedure, oxazoline compound (II) is contacted with an α, α-difluoroalkylamine fluorinating agent under pressure to give fluorinated oxazoline (III). Other alternative fluorinating agents can be employed, such as 1-diethylamino-1,1-difluoro-2-chloro-2-fluoro-ethane (FAR), phosphorus fluorides, hydrofluoric acid, an inorganic fluoride in a polyglycol and the like, as disclosed in U.S. Pat. No. 4,743,700 and European Patent Application 130,633, whose preparative teachings are incorporated herein by reference.

The following agent listed in these references are fluorides of alkali and alkaline earth metals, of ammonia, and phosphonium, phosphorus fluorides, hydrofluoric acid, FAR (1-diethylamino-1,1-difluoro-2-chloro-2-fluoro-ethane), an alpha, alphadifluoroalkylamine of the formula:

wherein
$X_1$ is chlorine or fluorine
$X_2$ is chlorine, fluorine or trifluoromethyl, R4 and R5 taken individually are lower alkyl, and
$R_4$ and $R_5$ taken together with the attached nitrogen atom represent the residue of a heterocyclic radical containing five to seven ring atoms.

A preferred fluorinating agent is Ishikawa reagent, defined previously.

In step (c), the desired compound (IV) can be prepared by hydrolyzing fluorinated compound (III) with an acid. In compound (IV), when Z=—SO$_2$CH$_3$, compound (IV) is known as florfenicol. Such acids can include but are not limited to hydrochloric, sulfuric, phosphoric, acetic, propionic and the like. The acid can be employed to adjust the pH of the reaction medium between 1 and 7, preferably at a pH of 4. Hydrolysis can be carried out at a temperature ranging from room temperature to the reflux temperature of the reaction medium. Compound (IV) can be recovered by conventional procedures, such as filtration, distillation, removal of any solvents present and crystallization. The following examples illustrate the present invention in a manner by which it can be practiced but, as such, should not be construed as limitations upon the overall scope of the same.

EXAMPLE 1.

Step (a)

Driving the equilibrium to D-(−)-threo-2-(dichloromethyl)-4,5-dihydro-5-[4-(methylsulfonyl)phenyl]-4-oxazolemethanol (II)

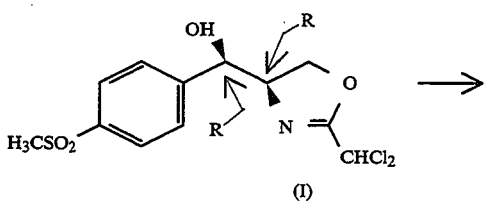

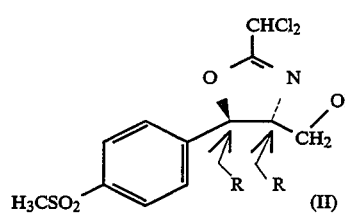

A slurry of 1.00 gram (g) of D-threo-2-(dichloromethyl)-4,5-dihydro-α-[4-(methylsulfonyl)phenyl]-4-oxazolemethanol (I) in 2 milliliters (ml) of isopropanol saturated with ammonia is stirred at a temperature of 80° C. for 2 hours (hr). With vigorous stirring 10 ml of n-heptane is added over a period of two minutes. The reaction mixture is then stirred at 60°-65° C. for 18 hr, cooled to 0°-5° C. and the solids are collected by filtration and washed with n-heptane and dried under vacuum at 50° C. to give 950 milligrams (mg) of the title compound (95 percent (%) yield).

Step (b)

Preparation of (4S,5R)-2-dichloromethyl-5-[4-(methylsulfonyl)phenyl]-4-fluoromethyl-1,3-oxazoline (III) by fluorination

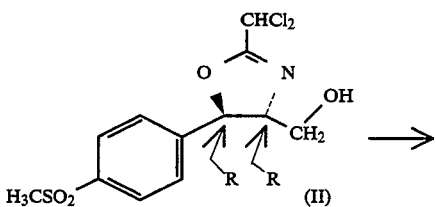

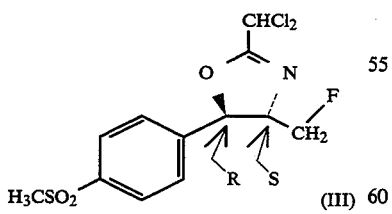

A 30 ml non-stirred pressure bomb equipped with a Teflon® insert (trademark of the DuPont E. Nemours Co., Wilmington Del.) is charged with 2.0 g D-(−)-threo-2-(dichloromethyl)-4,5-dihydro-5-[4-(methylsulfonyl)phenyl]-4-oxazolemethanol (II) from step (a). The bomb is then charged with 10 ml methylene chloride and 8.15 g Ishikawa reagent methylene chloride solution having an assay of 23.9% purity. The bomb is sealed, placed into an oil bath heated to 100° C. and heated for 2 hr. The bomb is removed from the oil bath, cooled to 0° C. in an ice/water bath and the contents containing the title compound (III) are transferred to a 250 ml round bottom flask equipped with a magnetic stirrer.

Step (c)

Preparation of [R-(R*,S*)]-2,2-dichloro-N-[1-(fluoromethyl)-2-hydroxy-2-[4-(methylsulfonyl)phenyl]ethylacetamide (IV) (ie. florfenicol) by hydrolysis

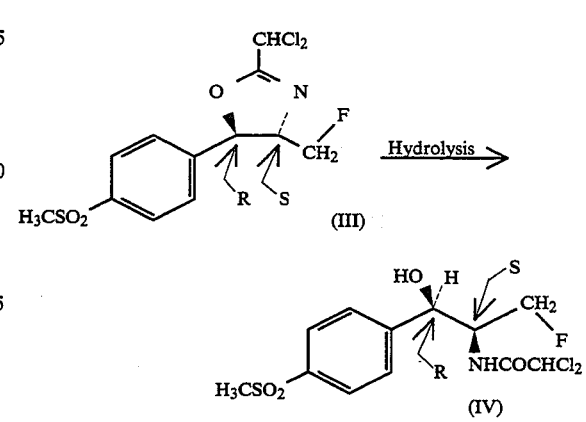

The 250 ml round-bottom flask in step (b) is charged with 0.15 g potassium acetate, 2.0 ml of methanol are added with agitation and the contents of the flask are concentrated under vacuum to one-half the volume. Ten milliliters of isopropanol/water (65:35, volume:-volume basis) are added to the flask and any remaining methylene chloride is removed by vacuum concentration. An additional 10 ml isopropanol/water (63:35) is added to the flask and the mixture is stirred at room temperature for 10 hr at pH 3.5 to 4.0. Hydrolysis of the (4S,5R)-2-dichloromethyl-5-[4-(methylsulfonyl)phenyl]-4-fluoromethyl- 1,3-oxazoline (III) is monitored by high pressure liquid chromatography (HPLC). The contents of the flask are concentrated over vacuum to one-half the volume to give a heavy precipitate, which is cooled overnight in a refrigerator. The precipitate is vacuum filtered, washed with 20 ml water, and dried at 50° C. under vacuum for 18 hr to give 1.93 g (85.7% yield)of title product (IV) having a purity of 90.9%.

EXAMPLE 2

Step (a)

Driving the equilibrium to D-(−)-threo-2-(dichloromethyl)-4,5-dihydro-5-[4-(methylsulfonyl)phenyl]-4-oxazolemethanol (II)

To a 30 ml isopropanol solution saturated with ammonia is added 20 g of D-(−)-threo-2-(dichloromethyl)-4,5-dihydro-α-[4-(methylsulfonyl)phenyl]-4-oxazolemethanol. The reaction mixture is stirred at 80° C. for 3 hours and then at 60° C. for 16 hours. After the reaction mixture is cooled to 5° C., the precipitates are filtered and washed with hexane to afford, after drying at 55° C. under vacuum, 17.3 g (88% yield) of the title compound (II) with a purity of 98.8%.

Step (b)

Preparation of (4S,5R)-2-dichloromethyl-5-[4-(methylsulfonyl)phenyl]-4-fluoromethyl-1,3-oxazoline (III) by fluorination A 300 ml non-stirred pressure bomb is charged sequentially with 38 g of D-(−)-threo-2-(dichloromethyl)-4,5-dihydro-5-[4-(methylsulfonyl)phenyl]-4-oxazolemethanol (II) from step (a), 155 ml of methylene chloride, 71 g of Ishikawa reagent methylene chloride solution having an assay 53% (weight/weight). The bomb is sealed, placed in a 100° C. oil bath and heated for 1.5 hours. The bomb is removed from the oil bath, cooled to 25° C. and the contents are transferred to a 500 ml separatory funnel containing 80 ml of water and 5 ml of 50% NaOH. The mixture is agitated and the layers are split. The organic layer is washed with another 60 ml of water. After separating the layers, the organic layer containing the title compound (III) is transferred to a 500 ml round bottom flask equipped with a stirrer.

Step (c)

Preparation of [R-(R*,S*)]-2,2-dichloro-N-[1-(fluoromethyl)-2-hydroxy-2-[4-( methylsulfonyl)phenyl]ethylacetamide (ie. florfenicol).

The organic layer from step (b) is concentrated under vacuum and 114 ml isopropanol and 76 ml of water are added to the flask. The pH of the isopropanol/water solution is adjusted to between 8.5 and 9.0 with ammonium hydroxide (NH₄OH) and the mixture is heated at 70°–75° C. for 15 minutes. Acetic acid is added to adjust the pH to between 4.0 and 5.0 and the mixture is heated to 70°–75° C. for 3 hours to hydrolyze the (4S,5 R)-2-dichloromethyl-5-[4-(methylsulfonyl)phenyl]-4-fluoromethyl-1,3-oxazoline (III). After the hydrolysis is completed, 80 ml of water are added and the mixture is agitated for 2 hours at 25° C. The precipitates are collected by filtration and washed with cold isopropanol/water (1:1) to give, after drying at 55° C. under vacuum for 16 hours, 33.63 g (82.1% yield) of the title compound (IV) with a purity of 98.4%.

PREPARATION OF STARTING MATERIALS

The oxazoline starting materials of formula (I) are known to those skilled in the art. Analogous methods for preparing oxazoline compound (I), particularly in admixture with oxazoline compound (II) are taught in U.S. Pat. Nos. 2,759,001 and 4,235,892, European Patent Application 130,633 and in H., Witte and Wolfgang Seeligar, Formation of Cyclic Imidic Esters by Nitriles with Amino Alcohols, Liebigs Ann. Chem. pp. 996–1009, (1974), whose preparative teachings are incorporated herein by reference.

A typical preparation is illustrated as follows:

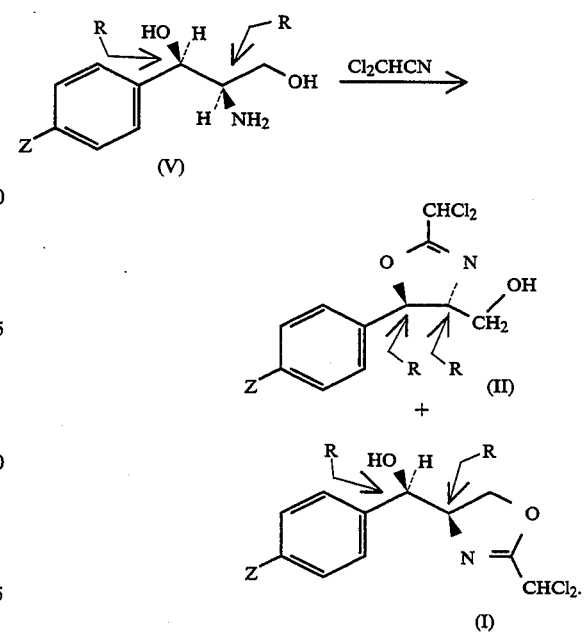

In the above illustration, oxazoline compound of formula (I) is prepared by contacting an aminodiol of formula (V) wherein Z is defined hereinbefore, preferably where Z=H₃CSO₂—, with dichloroacetonitrile and an alcohol, and optionally in the presence of a catalytic amount of an acid, to give a mixture containing oxazoline compounds (I) and (II). Suitable alcohols include the C-1 to C-10 alcohol such as methanol, ethanol, isopropanol and the like. Optionally and preferably a catalytic amount of an organic acid, ie. PTSA, acetic, and the like or a mineral acid mineral, ie. sulfuric, hydrochloric, phosphoric, and like can be employed. The reactants can be contacted at an temperature effective to prepare a mixture containing oxazoline compounds (I) and (II), generally between about 50°–80° C. The temperature can be raised or lowered to modify the purity of oxazolines (II) and (I) and their ratios. For example, the temperature of the reaction mixture can be heated to 70° C. for one to two hours and then lowered to 50° C. overnight to give a mixture of oxazolines (II) and (I), in which the amount of oxazoline (II) formed is greater than the amount of oxazoline (I).

Preparative Example.

Mixture of D-(−)-threo-2-(dichloromethyl)-4, 5-dihydro-5-[4-(methylsulfonyl)phenyl]-4-oxazolemethanol (II) and D-threo-2-(dichloromethyl)-4,5-dihydro-α-[4-( methylsulfonyl)phenyl]-4-oxazolemethanol (I)

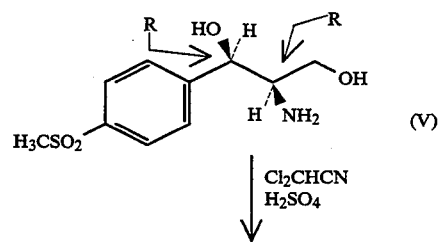

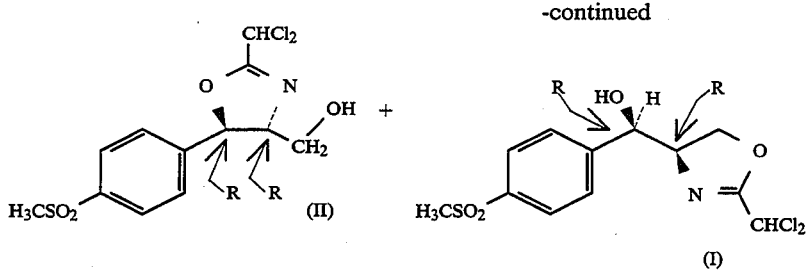

Equip a 500 ml 3-neck round bottom flask with an overhead stirrer, condenser, thermometer, nitrogen (N₂) overlay and baths for cooling and heating. Charge 130 ml of isopropanol to the flask. With agitation, charge 50.4 g dichloroacetonitrile to the flask and wash the residue in a weighing beaker with 20 ml of isopropanol into the flask. With agitation, charge 5 ml of concentrated sulfuric acid to the flask, maintaining the temperature less than 32° C. by use of an ice water bath. Cool to about 25° C. and charge 100 g D-(—)-threo-2-amino-1-[4-methylsulfonyl)phenyl]-1,3-propanediol to the reaction flask in amounts sufficient to maintain a smooth stirring. Heat the reaction slurry to 70° C. and maintain at this temperature for 1.5 hours to give title compounds (II) and (I) in a ratio of 70:30 (II:I).

What is claimed is:

1. A process for preparing a compound of formula (IV):

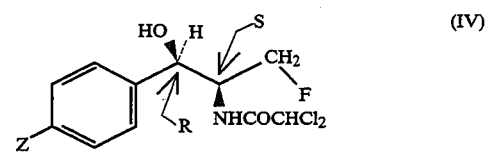

wherein Z represents H, halo, nitro or $H_3CSO_x^-$, wherein x is 0, 1 or 2, comprising a) contacting an oxazoline compound of formula (I):

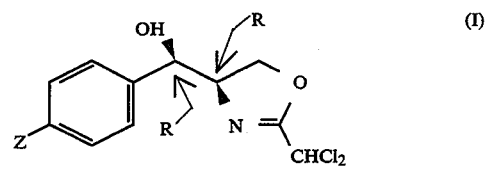

wherein Z is as defined hereinbefore, with sufficient quantity of an equilibrium driving reagent capable of causing an equilibrium between oxazoline compound (I) and an oxazoline compound of formula (II):

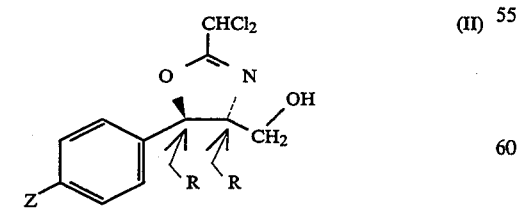

wherein Z is as defined hereinbefore, and the reagent drives the equilibrium toward oxazoline compound (II) by preferential precipitation of oxazoline compound (II) from the equilibrium driving reagent such that the molar ratio of compound (II) to compound (I) is at least 80:20; wherein the equilibrium driving reagent is selected from a protic solvent and ammonia or an ammonium salt, wherein the protic solvent consists essentially of water, a C-1 to C-10 alkanoic acid, a C-1 to C-10 alcohol or mixtures thereof; and recovering the so precipitated oxazoline compound;

b) contacting compound (II) with a fluorinating agent selected from the group consisting of fluorides of alkali and alkaline earth metals, fluorides of ammonia, fluorides of phosphonium, phosphorus fluoride, hydrofluoric acid, FAR (1-diethylamino-1,1-difluoro-2-chloro-2-fluoro-ethane), an alpha, alpha-difluoroalkylamine of the formula:

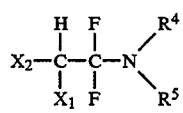

wherein $X_1$ is Chlorine or fluorine $X_2$ is chlorine, fluorine or trifluoromethyl, R4 and R,5 taken individually are lower alkyl, and R₄ and R₅ taken together with the attached nitrogen atom represent the residue of a heterocyclic radical having five to seven ring atoms and Ishikawa reagent, to give a fluorinated oxazoline compound of formula (III):

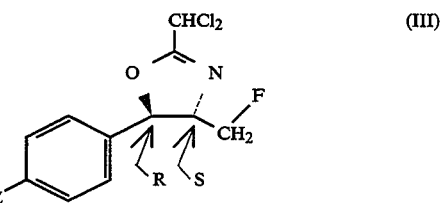

wherein Z is as defined hereinbefore; and c) hydrolyzing compound (III) to compound (IV).

2. The process of claim 1 wherein a cosolvent selected from the group consisting of $C_{4-C10}$ alkanes, benzene, toluene, xylenes, chlorobenzene, diethylether, tert-butylmethylether, isopropylether and mixtures thereof is present in the equilibrium driving agent.

3. A process for preparing an oxazoline compound of formula (II):

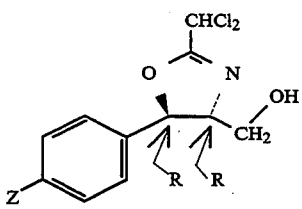

wherein Z represents H, halo, nitro or $H_3CSO_x^-$, wherein x is 0, 1 or 2, comprising contacting an oxazoline compound of formula (I):

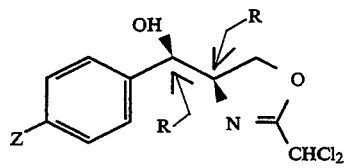

wherein Z is as defined herein before, with sufficient quantity of an equilibrium driving reagent capable of causing an equilibrium between oxazoline compound (I) and oxazoline compound (II), wherein the reagent drives the equilibrium toward oxazoline compound (II) by preferential precipitation of oxazoline compound (II) from the equilibrium driving reagent such that the molar ratio of compound (II) to compound (I) is at least 80:20; wherein the equilibrium driving reagent is selected from a protic solvent and ammonia or an ammonium salt, wherein the protic solvent consists essentially of water, a C-1 to C-10 alkanoic acid, a C-1 to C-10 alcohol or mixtures thereof; and recovering the so precipitated oxazoline compound.

4. The process of claim 3 wherein a cosolvent selected from the group consisting of $C_4-C_{10}$ alkanes, benzene, toluene, xylenes, chlorobenzene, diethylether, tert-butylmethylether, isopropylether and mixtures thereof is present in the equilibrium driving agent.

5. The process of claim 1 wherein the protic solvent comprises isopropyl alcohol.

6. The process of claim 5 wherein the isopropanol is present in an amount of from 1.5 to 2 ml of isopropanol per gram of oxazoline (I).

7. The process of claim 1 wherein oxazoline (II) is recovered by filtering precipitated oxazoline (II) from the reaction mixture.

8. The process of claim 1 wherein oxazoline compound (I) is admixed with oxazoline compound (II) prior to contacting with the equilibrium driving reagent.

9. The process of claim 3 wherein the protic solvent comprises isopropyl alcohol.

10. The process of claim 9 wherein the isopropanol is present in an amount of from 1.5 to 2 ml of isopropanol per gram of oxazoline (I).

11. The process of claim 3 wherein Z represents $H_3CSO_2-$.

12. The process of claim 3 wherein oxazoline (II) is recovered by filtering precipitated oxazoline (II) from the reaction mixture.

13. The process of claim 3 wherein oxazoline compound (I) is admixed with oxazoline compound (II) prior to contacting with the equilibrium driving reagent.

14. The process of claim 1 Z represents $H_3CSO_2-$.

* * * * *